US012766177B2

(12) United States Patent
Shyur et al.

(10) Patent No.: US 12,766,177 B2

(45) Date of Patent: Oct. 20, 2026

(54) **USE OF *Crassocephalum rabens* EXTRACT IN THE PREVENTION AND/OR TREATMENT OF FATIGUE AND/OR DEPRESSION**

(71) Applicant: ACADEMIA SINICA, Taipei (TW)

(72) Inventors: Lie-Fen Shyur, Taipei (TW); Yu-Chuan Liang, Taipei City (TW); Yu-Hsin Chen, Taichung City (TW); Chuan-Ju Lin, New Taipei City (TW); Meng-Ting Chang, Kaohsiung City (TW); Chung-Chih Yang, Xihu Township (TW)

(73) Assignee: ACADEMIA SINICA, Taipei (TW)

( * ) Notice: Subject to any disclaimer, the term of this patent is extended or adjusted under 35 U.S.C. 154(b) by 455 days.

(21) Appl. No.: 18/253,662

(22) PCT Filed: Nov. 19, 2021

(86) PCT No.: PCT/US2021/072518

§ 371 (c)(1),
(2) Date: May 19, 2023

(87) PCT Pub. No.: WO2022/109602

PCT Pub. Date: May 27, 2022

(65) Prior Publication Data

US 2024/0009259 A1 Jan. 11, 2024

Related U.S. Application Data

(60) Provisional application No. 63/116,662, filed on Nov. 20, 2020.

(51) Int. Cl.

*A61K 36/28* (2006.01)
*A61K 31/7028* (2006.01)
*A61P 21/00* (2006.01)
*A61P 25/24* (2006.01)

(52) U.S. Cl.

CPC .......... *A61K 36/28* (2013.01); *A61K 31/7028* (2013.01); *A61P 21/00* (2018.01); *A61P 25/24* (2018.01)

(58) Field of Classification Search

CPC ................ A61K 36/28; A61K 31/7028; A61K 31/7034; A61P 21/00; A61P 25/24; A61P 25/28; A61P 25/00; A61P 43/00

See application file for complete search history.

(56) References Cited

U.S. PATENT DOCUMENTS

| | | | | |
|---|---|---|---|---|
| 2008/0152737 | A1* | 6/2008 | Shyur | A61K 36/41 435/375 |
| 2009/0291134 | A1 | 11/2009 | Ahmad et al. | |
| 2014/0356301 | A1* | 12/2014 | Shyur | A61P 1/16 424/62 |

FOREIGN PATENT DOCUMENTS

| | | | | |
|---|---|---|---|---|
| CN | 106413753 A | | 2/2017 | |
| ES | 2759878 | | 5/2020 | |
| SG | 11202007005 A | | 8/2020 | |
| TW | 201932136 A | | 8/2019 | |
| WO | 2019021008 A1 | | 1/2019 | |
| WO | WO-2019147300 A1 | * | 8/2019 | A61K 31/7032 |

OTHER PUBLICATIONS

Sanjeev Karmakar., et al. Anti-Inflammatory, Immunomodulatory and Antigenotoxic Potential of Crassocephalum crepidioides (Benth.) S. Moore Methanolic Extract. EC Pharmacology and Toxicology 6.4 (2018): 296-315, 20 pages. <https://ecronicon.net/assets/ecpt/pdf/ECPT-06-00163.pdf>. (Year: 2018).*

Adler, R.H., "Chronic fatigue syndrome," Swiss Med. Wkly. 2004, 134, 268-276.

Apaya, M. K. et al., "Deregulating the CYP2C19/Epoxy-Eicosatrienoic Acid-Associated FABP4/FABP5 Signaling Network as a Therapeutic Approach for Metastatic Triple-Negative Breast Cancer," Cancers 2020, 12, 199.

Apaya, M. K. et al., "Simvastatin and a Plant Galactolipid Protect Animals from Septic Shock by Regulating Oxylipin Mediator Dynamics through the MAPK-cPLA(2) Signaling Pathway," Mol Med. 2015, 21, 988-1001.

Belluardo, N et al., "Neuromuscular Junction Disassembly and Muscle Fatigue in Mice Lacking Neurotrophin-4," Mol. Cell. Neurosci. 2001, 18, 56-67.

Chaudhuri, A. and Behan, P.O., "Fatigue in neurological disorders," Lancet. 2004, 363, 978-988.

Hou, C.-C. et al., "A Galactolipid Possesses Novel Cancer Chemopreventive Effects by Suppressing Inflammatory Mediators and Mouse B16 Melanoma," Cancer Res. 2007, 67, 6907-6915.

https://www.agriharvest.tw/archives/40373. Downloaded on Dec. 2, 2022. English translation provided.

https://z.xiziwang.net/shucai/62172/. Downloaded Dec. 2, 2022. English translation provided.

Kim, NH et al., "Anti-Fatigue Effect of Zizania caudiflora (Turczaninow) Nakai," Am J Chin Med. 2012, 40, 111-120.

Li X, et al., "Leptin Increases Expression of 5-HT(2B) Receptors in Astrocytes Thus Enhancing Action of Fluoxetine on the Depressive Behavior Induced by Sleep Deprivation," Front Psychiatry. 2019, 9, 734.

M. Kosari-Nasab et al., "Anxiolytic- and antidepressant-like effects of silymarin compared to diazepam and fluoxetine in a mouse model of mild traumatic brain injury," Toxicology and Applied Pharmacology. 2018, 338, 159-173.

(Continued)

*Primary Examiner* — Aaron J Kosar
*Assistant Examiner* — Jennifer Lynn Cain
(74) *Attorney, Agent, or Firm* — Prosyla Group, PC

(57) ABSTRACT

The present disclosure provides a method for preventing and/or treating fatigue and/or depression in a subject in need of such prevention and/or treatment, comprising administering to said subject an effective amount of *Crassocephalum rabens* plant or extract and optionally a pharmaceutically acceptable carrier or excipient. The present disclosure also provides a method for increasing skeletal muscle lactate dehydrogenase and/or malate dehydrogenase.

6 Claims, 9 Drawing Sheets

(56) References Cited

OTHER PUBLICATIONS

Office Action and Search Report issued in Taiwan Patent Application No. 110143161 dated Dec. 9, 2022. English translation of Search Report.
Rollnik JD., "Das chronische Muedigkeitssyndrom—ein kritischer Diskurs (Chronic Fatigue Syndrome: A Critical Review)" Fortschr Neurol Psychiatr. 2017, 85, 79-85.
Xia, F. et al., "Antioxidant and Anti-Fatigue Constituents of Okra," Nutrients. 2015, 7, 8846-8858.
Zhong, L. et al., "Evaluation of anti-fatigue property of the extruded product of cereal grains mixed with Cordyceps militaris on mice," J Intern Soc Sports Nutri. 2017, 14, 159-12.
International Search Report and Written Opinion issued on Feb. 18, 2022 in Application No. PCT/US21/72518.
Ki, Hyeon-Hui et al., "In vitro and in vivo anti-cancer activity in dichloromethane fraction of Triticum aestivum spouts," Biomedicine & Pharmacotherapy, (2017), vol. 96, pp. 120-128. Elsevier. col. 2, paragraph 1.
Yang, "Plant galactolipid dLGG suppresses lung metastasis of melanoma through deregulating TNF-[alpha]-mediated pulmonary vascular permeability and circulating oxylipin dynamics in mice," International Journal of Cancer, 2018, p. 3254; col. 2, paragraph 3; DOI:10.1002/ijc31663.

* cited by examiner

USE OF *Crassocephalum rabens* EXTRACT IN THE PREVENTION AND/OR TREATMENT OF FATIGUE AND/OR DEPRESSION

PRIORITY DATA

This application is a 371 U.S. National Phase of International Patent Application No. PCT/US21/72518, filed Nov. 19, 2021, which claims priority to and benefit of U.S. Provisional Patent Application No. 63/116,662, filed Nov. 20, 2020, the contents of which are incorporated in their entirety herewith.

BACKGROUND

1. Field of the Disclosure

The present disclosure relates to use of *Crassocephalum rabens*, and more particularly to use of *Crassocephalum rabens* in the prevention and/or treatment of fatigue and/or depression.

2. Description of the Related Art

Fatigue is defined as "difficulty in initiating or sustaining voluntary activities," which is a complex physiological phenomenon (Chaudhuri, A. and Behan, P. O., Lancet. 2004, 363, 978-988.). Fatigue is becoming a more common symptom in normal humans, and it has also been observed in association with several disorders or physiological conditions in humans, including age, cancer, depression, HIV infection, Parkinson's disease (Belluardo, N et al., Mol. Cell. Neurosci. 2001, 18, 56-67). However, depression is not only a common disorder of chronic fatigue symptoms, but is also a risk factor for the development of neurotic diseases in clinical patients, such as Alzheimer's disease and mild traumatic brain injury (Rollnik J D., Fortschr Neurol Psychiatr. 2017, 85, 79-85; Li X, et al., Front Psychiatry. 2019, 9, 734; M. Kosari-Nasab et al., Toxicology and Applied Pharmacology. 2018, 338, 159-173). Chronic fatigue syndrome patients were found to have higher instances of depression (Adler, R. H. Chronic fatigue syndrome. Swiss Med. Wkly. 2004, 134, 268-276).

*C. rabens* (CR) (also named *C. crepidioides*) extracts and its derived bioactive galactolipid, 1,2-di-O-linolenoyl-3-O-β-galactopyranosyl-sn-glycerol (dLGG) or galactolipid-enriched fraction have been shown with potent activity against sepsis in mice (Apaya, M. K. et al., Mol Med. 2015, 21, 988-1001), anti-inflammatory and cancer chemopreventive effects against melanoma growth and lung metastasis (Yang, C.-C. et al., Int J Cancer. 2018, 143, 3248-3261; Hou, C.-C. et al., Cancer Res. 2007, 67, 6907-6915), and also effectively attenuated triple negative breast cancer recurrence and lung metastasis through deregulating the FABP/EET dynamics and levels in syngeneic or xenograft mouse models (Apaya, M. K. et al., Cancers 2020, 12, 199).

SUMMARY

The present disclosure provides use of *Crassocephalum rabens* plant or extract in the prevention and/or treatment of fatigue and/or depression. This is the first use of *Crassocephalum rabens* plant or extract as an anti-fatigue agent and potential anti-depressant.

The present disclosure provides a method for preventing and/or treating fatigue in a subject in need of such prevention and/or treatment, comprising administering to said subject an effective amount of *Crassocephalum rabens* plant or extract and optionally a pharmaceutically acceptable carrier or excipient.

In one embodiment of the disclosure, the *Crassocephalum rabens* is *Crassocephalum rabens* S. Moore (Asteraceae).

In one embodiment of the disclosure, the *Crassocephalum rabens* plant is pieces of dried *Crassocephalum rabens*.

In one embodiment of the disclosure, the *Crassocephalum rabens* extract is liquid of *Crassocephalum rabens*.

In one embodiment of the disclosure, the fatigue is associated with a disease, disorder or condition selected from the group consisting of depression, cancer, multiple sclerosis, Parkinson's disease, Alzheimer's disease, chronic fatigue syndrome, fibromyalgia, chronic pain, traumatic brain injury, AIDS, and osteoarthritis.

In another embodiment, the fatigue is associated with a particular treatment or therapy used to treat a disease, disorder, or condition, including, without limitation, chemotherapy, radiation therapy, bone marrow transplant, and anti-depressant medications.

In one embodiment of the disclosure, the fatigue is chronic or acute fatigue.

The present disclosure provides a method for increasing skeletal muscle lactate dehydrogenase and/or malate dehydrogenase in a subject in need of such increase, comprising administering to said subject an effective amount of *Crassocephalum rabens* plant or extract and optionally a pharmaceutically acceptable carrier or excipient.

The present disclosure also provides a method for preventing and/or treating fatigue in a subject in need of such prevention and/or treatment, comprising administering to said subject an effective amount of galactolipid compounds from *Crassocephalum rabens* or a pharmaceutically acceptable derivative thereof and optionally a pharmaceutically acceptable carrier or excipient.

In one embodiment of the disclosure, the galactolipid compound is 1,2-di-O-α-linolenoyl-3-O-β-galactopyranosyl-sn-glycerol (dLGG) or 1,2-di-(α-linolenoyl)-3-[α-D-galactosyl-(1-6)-β-D-galactosyl]-sn-glycerol (DGDG).

The present disclosure also provides a method for increasing skeletal muscle lactate dehydrogenase and/or malate dehydrogenase in a subject in need of such increase, comprising administering to said subject an effective amount of galactolipid compounds from *Crassocephalum rabens* or a pharmaceutically acceptable derivative thereof, and optionally a pharmaceutically acceptable carrier or excipient.

The present disclosure also provides a method for preventing and/or treating depression in a subject in need of such prevention and/or treatment, comprising administering to said subject an effective amount of *Crassocephalum rabens* plant or extract and optionally a pharmaceutically acceptable carrier or excipient.

In one embodiment of the disclosure, the depression is selected from the group consisting of major depressive disorder; bipolar I disorder; bipolar II disorder; mixed state bipolar disorder; dysthymic disorder; rapid cycler; atypical depression; seasonal affective disorder; postpartum depression; hypomelancholia; recurrent brief depressive disorder; refractory depression; chronic depression; double depression; alcohol-induced mood disorder; mixed anxiety-depressive disorder; depression caused by a physical disease, selected from the group consisting of Cushing('s) syndrome, hypothyroidism, hyperparathyroidism, Addison's disease, amenorrhea-galactorrhea syndrome, Parkinson's disease, Alzheimer's disease, cerebrovascular dementia, brain infarct, brain hemorrhage, subarachnoid hemorrhage, diabetes millitus, viral infection, multiple sclerosis, chronic fatigue syndrome, coronary artery disease, pain, and cancer; presenile depression; senile depression; depression in children and adolescents; and depression induced by drugs.

The present disclosure also provides a method for preventing and/or treating depression in a subject in need of such prevention and/or treatment, comprising administering to said subject an effective amount of galactolipid compounds from *Crassocephalum rabens* or a pharmaceutically acceptable derivative thereof, and optionally a pharmaceutically acceptable carrier or excipient.

The present invention is described in detail in the following sections. Other characteristics, purposes and advantages of the present invention can be found in the detailed description and claims.

DETAILED DESCRIPTION

Figure 1:
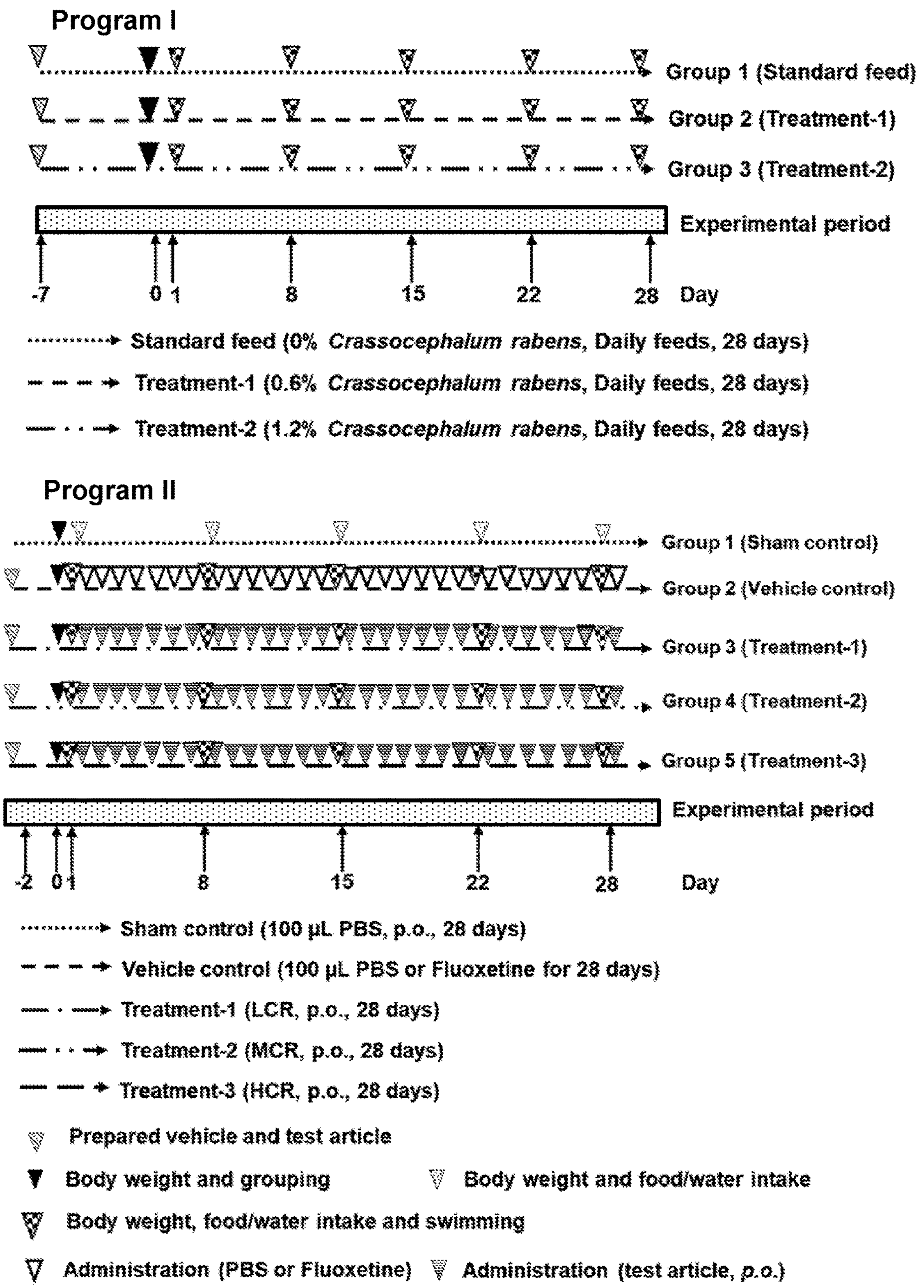
FIG. 1 shows programs I and II of anti-fatigue experimental designs in mice. Schematic diagram of the experimental design in BALB/c mice fed with *Crassocephalum rabens* plant powder (CR). All BALB/c mice, aged 4-5 weeks, were randomly assigned into treated or non-treated groups, and 5 males or females per group. In program I, each group was fed a standard diet (0% CR) or a standard diet containing 0.6% CR or 1.2% CR for 4 weeks. In program II, oral gavages were administered with *C. rabens* extract (CRE) at a dose of 150 mg/kg BW, 300 mg/kg BW or 600 mg/kg BW for 4 weeks. Mice were given PBS as a control group for four weeks.

The present invention can be more readily understood by reference to the following detailed description of various embodiments of the invention, the examples, and the chemical drawings and tables with their relevant descriptions. It is to be understood that unless otherwise specifically indicated by the claims, the invention is not limited to specific preparation methods, carriers or formulations, or to particular modes of formulating the extract of the invention into products or compositions intended for topical, oral or parenteral administration, because as one of ordinary skill in the relevant arts is well aware, such things can, of course, vary. It is also to be understood that the terminology used herein is for the purpose of describing particular embodiments only, and is not intended to be limiting.

As utilized in accordance with the present disclosure, the following terms, unless otherwise indicated, shall be understood to have the following meaning:

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

As used herein, the term "or" is used to mean "and/or" unless explicitly indicated to refer to alternatives only, or the alternatives are mutually exclusive.

As used herein, the terms "subject" and "patient" are used interchangeably herein and will be understood to refer to a warm blooded animal, particularly a mammal. Non-limiting examples of animals within the scope and meaning of this term include guinea pigs, dogs, cats, rats, mice, horses, goats, cattle, sheep, zoo animals, non-human primates, and humans.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "preventing" or "prevention" is recognized in the art, and when used in relation to a condition, it includes administering, prior to onset of the condition, an agent to reduce the frequency or severity of or to delay the onset of symptoms of a medical condition in a subject, relative to a subject which does not receive the agent.

The term "treating" or "treatment" as used herein denotes reversing, alleviating, inhibiting the progress of, or improving the disorder, disease or condition to which such term applies, or one or more symptoms of such disorder, disease or condition.

The term "fatigue" is understood in the art and is generally defined as a condition characterized by a lessened capacity for work and reduced efficiency of accomplishment, usually accompanied by a feeling of weariness and tiredness as well as lack of mental sharpness, focus and concentration. Fatigue can either be acute or chronic. Fatigue is distinguished from sleepiness and disorders associated with sleepiness (such as excessive daytime sleepiness and narcolepsy). Fatigue is also distinguished from tiredness due to a lack of adequate sleep.

The terms "fatigue associated with diseases or treatments" and "associated with fatigue" (and similar terms), as used herein, refer to any disease, disorder, condition, treatment, or medication that has fatigue as one of its symptoms or side effects.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve the appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The term "a pharmaceutically acceptable derivative" or "pharmaceutically acceptable derivatives" as used herein denotes a compound that is modified from the compound of the invention but has properties and efficacies that are the same as or better than those of the compound of the invention. Preferably, the pharmaceutically acceptable derivative is a pharmaceutically acceptable salt, solvate, hydrate, or prodrug of the compound of the invention.

The compounds of the invention can also exist as solvates and hydrates. Thus, these compounds may crystallize with, for example, waters of hydration, or one, a number of, or any fraction of molecules of the mother liquor solvent. The solvates and hydrates of such compounds are included within the scope of this invention.

The present disclosure provides a method for preventing and/or treating fatigue in a subject in need of such prevention and/or treatment, comprising administering to said subject an effective amount of *Crassocephalum rabens* plant or extract and optionally a pharmaceutically acceptable carrier or excipient.

The *Crassocephalum rabens* according to the disclosure is also known as *C. rabens* S. Moore, *C. rubens* S. Moore, *C. crepidioides* S. Moore, and *Crassocephalum crepidioides*. In one embodiment of the disclosure, the *Crassocephalum rabens* is *Crassocephalum rabens* S. Moore (Asteraceae). As used herein, the *Crassocephalum rabens* plant may be the whole plant or one or more parts thereof, including but not limited to, seeds, flowers, leaves, stems and roots. In an embodiment of the present invention, the *Crassocephalum rabens* plant is the whole plant. In another embodiment of the present invention, the *Crassocephalum rabens* plant is seeds, flowers, leaves, or any combination thereof.

The *Crassocephalum rabens* plant may be collected at various stages.

In one embodiment of the disclosure, the *Crassocephalum rabens* plant is a mixture obtained by removing some substances from the *Crassocephalum rabens*. In a preferred embodiment of the present invention, the *Crassocephalum rabens* plant is prepared by drying and crushing the *Crassocephalum rabens*, and is pieces of dried *Crassocephalum rabens*.

In a preferred embodiment of the present invention, the *Crassocephalum rabens* extract is prepared by removing solid contents of the *Crassocephalum rabens* and the *Crassocephalum rabens* extract is liquid of *Crassocephalum rabens*.

The anti-fatigue activity of pieces of dried *Crassocephalum rabens* (CR) and liquid extract of *Crassocephalum rabens* (CRE) is provided using exhaustive mouse swimming models. The forced swimming test is popularly used as an endurance experimental system to examine anti-fatigue effect and also as a screening platform for anti-depressant properties of bioactive agents (Adler, R. H., Swiss Med. Wkly. 2004, 134, 268-276). Several studies used forced swimming exercise to examine the behavioral despair in animals in tandem with evaluating the anti-fatigue properties of novel plant derived bioactive compounds (Kim, N H et al., Am J Chin Med. 2012, 40, 111-120; Nishizawa, K et al., Biol Pharm Bull. 2007, 30, 1758-1762; Xia, F. et al., Nutrients. 2015, 7, 8846-8858; Zhong, L. et al., J Intern Soc Sports Nutri. 2017, 14, 159-12). In the anti-fatigue animal studies, CR were administered as a form of feed additive for 28 days, CRE was orally administered once a day for 28 days, or the control drug Fluoxetine (10 mg/kg) was administered intraperitoneally every day on BALB/c mice. The swimming abilities of individual mice were tested, and skeletal muscle glycogen content, lactate dehydrogenase (LDH), and malate dehydrogenase (MDH) activities were evaluated as an indicator of mouse skeletal muscle ability. The results show that both feed additive treated group with CR and CRE treated group by oral gavage all significantly prolonged the mice swimming duration, and CRE effect was better than the control drug Fluoxetine. In male mice, the CR feed additive and CRE oral gavage groups were all observed with dose-dependent and significantly increased skeletal muscle LDH and MDH activities. In conclusion, the novel anti-fatigue efficacy of *C. rabens* extract is confirmed through promotion of swimming time/capability and the skeletal LDH and MDH activities in mice.

In one embodiment of the disclosure, the fatigue is associated with a disease, disorder or condition selected from the group consisting of depression, cancer, multiple sclerosis, Parkinson's disease, Alzheimer's disease, chronic fatigue syndrome, fibromyalgia, chronic pain, traumatic brain injury, AIDS, and osteoarthritis.

In another embodiment, the fatigue is associated with a particular treatment or therapy used to treat a disease, disorder, or condition, including, without limitation, chemotherapy, radiation therapy, bone marrow transplant, and anti-depressant medications.

In one embodiment of the disclosure, the fatigue is chronic or acute fatigue.

The present disclosure provides a method for increasing skeletal muscle lactate dehydrogenase and/or malate dehydrogenase in a subject in need of such increase, comprising administering to said subject an effective amount of *Crassocephalum rabens* plant or extract and optionally a pharmaceutically acceptable carrier or excipient.

The present disclosure also provides a method for preventing and/or treating fatigue and/or depression in a subject in need of such prevention and/or treatment, comprising administering to said subject an effective amount of galactolipid compounds from *Crassocephalum rabens* or a pharmaceutically acceptable derivative thereof, and optionally a pharmaceutically acceptable carrier or excipient.

The galactolipid compounds from the *Crassocephalum rabens* includes, but is not limited to, 1,2-di-O-α-linolenoyl-3-O-β-galactopyranosyl-sn-glycerol (dLGG), and 1,2-di-(α-linolenoyl)-3-[α-D-galactosyl-(1-6)-β-D-galactosyl]-sn-glycerol (DGDG). In one preferred embodiment of the disclosure, the galactolipid compound is 1,2-di-O-α-linolenoyl-3-O-β-galactopyranosyl-sn-glycerol.

The galactolipid compounds of the disclosure can be further converted into a pharmaceutically acceptable derivative, such as a pharmaceutically acceptable salt, solvate or prodrug, by any known methods.

The present disclosure also provides a method for increasing skeletal muscle lactate dehydrogenase and/or malate dehydrogenase in a subject in need of such increase, comprising administering to said subject an effective amount of galactolipid compounds from *Crassocephalum rabens* or a pharmaceutically acceptable derivative thereof, and optionally a pharmaceutically acceptable carrier or excipient.

The present disclosure also provides a method for preventing and/or treating depression in a subject in need of such prevention and/or treatment, comprising administering to said subject an effective amount of *Crassocephalum rabens* plant or extract, and optionally a pharmaceutically acceptable carrier or excipient.

In one embodiment of the disclosure, the depression is selected from the group consisting of major depressive disorder; bipolar I disorder; bipolar II disorder; mixed state bipolar disorder; dysthymic disorder; rapid cycler; atypical depression; seasonal affective disorder; postpartum depression; hypomelancholia; recurrent brief depressive disorder; refractory depression; chronic depression; double depression; alcohol-induced mood disorder; mixed anxiety-depressive disorder; depression caused by a physical disease, selected from the group consisting of Cushing('s) syndrome, hypothyroidism, hyperparathyroidism, Addison's disease, amenorrhea-galactorrhea syndrome, Parkinson's disease, Alzheimer's disease, cerebrovascular dementia, brain infarct, brain hemorrhage, subarachnoid hemorrhage, diabetes millitus, viral infection, multiple sclerosis, chronic fatigue syndrome, coronary artery disease, pain, and cancer; presenile depression; senile depression; depression in children and adolescents; and depression induced by drugs.

The present disclosure also provides a method for preventing and/or treating depression in a subject in need of such prevention and/or treatment, comprising administering to said subject an effective amount of galactolipid compounds from *Crassocephalum rabens* or a pharmaceutically acceptable derivative thereof, and optionally a pharmaceutically acceptable carrier or excipient.

The *Crassocephalum rabens* extract is preferably contained in an extraction composition.

The extraction composition according to the invention is preferably a pharmaceutical composition or food composition.

The pharmaceutical composition according to the invention is preferably administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream, or a combination thereof. If necessary, it may be sterilized or mixed with any pharmaceutically acceptable carrier or excipient, many of which are known to one of ordinary skill in the art.

The extract composition can be added to a conventional food composition (i.e., the edible food or drink or precursors thereof) in the manufacturing process of the food composition. Almost all food compositions can be supplemented with the extract composition of the invention. The food compositions that can be supplemented with the extract composition of the invention include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The following Examples are given for the purpose of illustration only and are not intended to limit the scope of the present invention.

Example: *Crassocephalum rabens* Extract and Containing Galactolipid Compounds for Preventing and/or Treating Fatigue and/or Depression

Materials and Methods

Preparation of *Crassocephalum rabens* Plant Powder and Extract

The flower-blooming stage of *C. rabens* S. Moore (Asteraceae) (also known as *C. crepidioides* S. Moore) plants were harvested and dried out at temperatures of 60-65 °C. The dried plants (CR) were then crushed, passed through a 20 mesh sieve (<830 m) and ready for study. Meanwhile, another batch of the fresh *C. rabens* plants was subjected to preparing fresh pressed juice by physical force to yield CR extract (CRE). The fresh-pressed CRE was then incubated at temperatures of 60-65 °C until completely dried out for the following study. The quality of batch-to-batch CR and CRE were monitored by HPLC or basic nutritional factors analysis.

Reagents

All chemicals and solvents were used as purchased. Fluoxetine (fluoxetine hydrochloride) used as a positive/reference compound was purchased from Sigma (MO, USA). All solvents were of reagent or high-pressure liquid chromatography (HPLC) grade.

Animals

BALB/c strain mice were maintained in Laboratory Animal Core Facility, Agricultural Biotechnology Research Center, Academia *Sinica* and used in accordance with IACUC guidelines. Mice about 3 weeks of age and weighing 10-12 g were forced to swim three times to get accustomed to swimming. The *C. rabens* anti-fatigue experiment was carried out in two designed programs summarized in FIG. 1. Program I was a course of four consecutive study weeks using three groups of mice and each group included 5 mice (n=5). Each mouse was fed forages which contain two different doses of crushed *C. rabens* plant powder as feed additives (low dose 0.6% and high dose 1.2%) for 28 days. Mice were feed regular feeds as a control group. Program II was a course lasting four consecutive study weeks using five groups of mice (n=5 in each group). Mice were oral gavaged with *C. rabens* extract ("CRE") every day at a dose of 150 mg/kg BW (LCRE), 300 mg/kg BW (MCRE) or 600 mg/kg BW (HCRE) for 4 weeks, or injected intraperitoneally with the control drug Fluoxetine (10 mg/kg) every day (Kim, N H et al., Am J Chin Med. 2012, 40, 111-120). Mice were given PBS for four weeks as the vehicle control group, or fed by regular diet as the sham control. Individual mouse body weight and swimming ability were taken once a week in the program I and program II experiments. Mice were monitored daily for signs of potential toxicity and morbidity; any abnormal findings were recorded.

Animal Forced Swimming Test (FST)

Individual animal swimming ability test was taken one time per week in program I or two times per week in program II. For this experiment, a glass container 25 cm in length and 12 cm in diameter was filled up to 8 cm with water at 25 °C and the mice were gently released into the water from 20 cm above. The discontinuation of the movement of the mice limbs was considered immobility. The experiment was conducted for all groups between 9 am and 4 pm under similar conditions. The forced swimming test lasted a total of 6 minutes. The first two minutes were considered the adjustment time to the conditions for the mice, and their immobility during this period of time was not recorded. Immobility was recorded for the next 4 minutes.

LDH and MDH Activities and Glycogen Content in Skeletal Muscle

Skeletal muscle lactate dehydrogenase and malate dehydrogenase activities and glycogen content were determined after animal dissection using commercially available colorimetric determination kits from BioVison (CA, USA).

Blood Biochemical Parameters

Cardiac blood was collected in vacutainers without anticoagulant for biochemical estimation. Mice sera were analyzed using a Dri-Chem 4000i analyzer (Fuji, Tokyo, Japan) for the levels of GOT, glutamic oxaloacetic transaminase; GPT, glutamic pyruvic transaminase; LDH, lactate dehydrogenase; ALP, alkaline phosphatase; GLU, glucose; BUN, blood urea nitrogen; CTE, creatinine; UA, uric acid; CHO, cholesterol; HDL, High-density lipoprotein; TG, triglyceride; TBIL, total bilirubin; TP, total protein; ALB, albumin; GLOB, globulin; A/G ratio, albumin-globulin in ratio.

Statistical Analysis

All data were analyzed using STATRAPHIC plus software by Statistical Graphics Corp. Values are presented as mean±standard deviation (S.D.). A Student's t-test was used to evaluate the differences between control and treatment groups. A significance level of 5% was adopted for the analysis.

Results and Discussion

*C. rabens* (CR) Treatment Increased Forced Swimming Capacity in Mice

Figure 2:
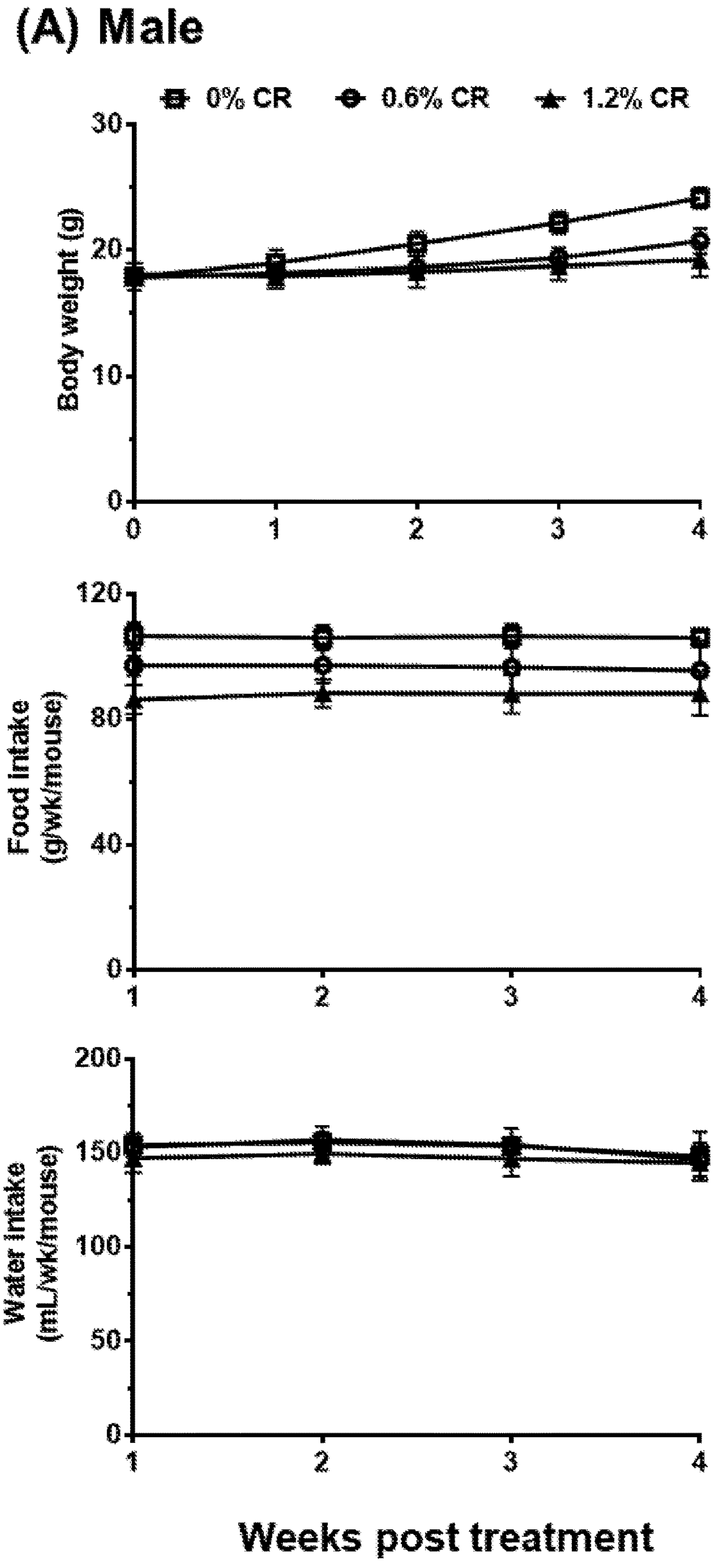
FIGS. 2 (A) and 2 (B) show body weight, food consumption and water intake of BALB/c mice fed with *Crassocephalum rabens* plant. In the program I study, male (A) and female (B) BALB/c mice, aged 4-5 weeks, were randomly assigned into 3 groups (n=5 in each group). One group was fed a standard diet (0% CR), and the other two groups were fed a standard diet containing 0.6% CR and 1.2% CR for 4 weeks. Values are expressed as the mean±S.D. *p<0.05 as compared with the control group (0% CR), which is considered to be significant.
Figure 2:
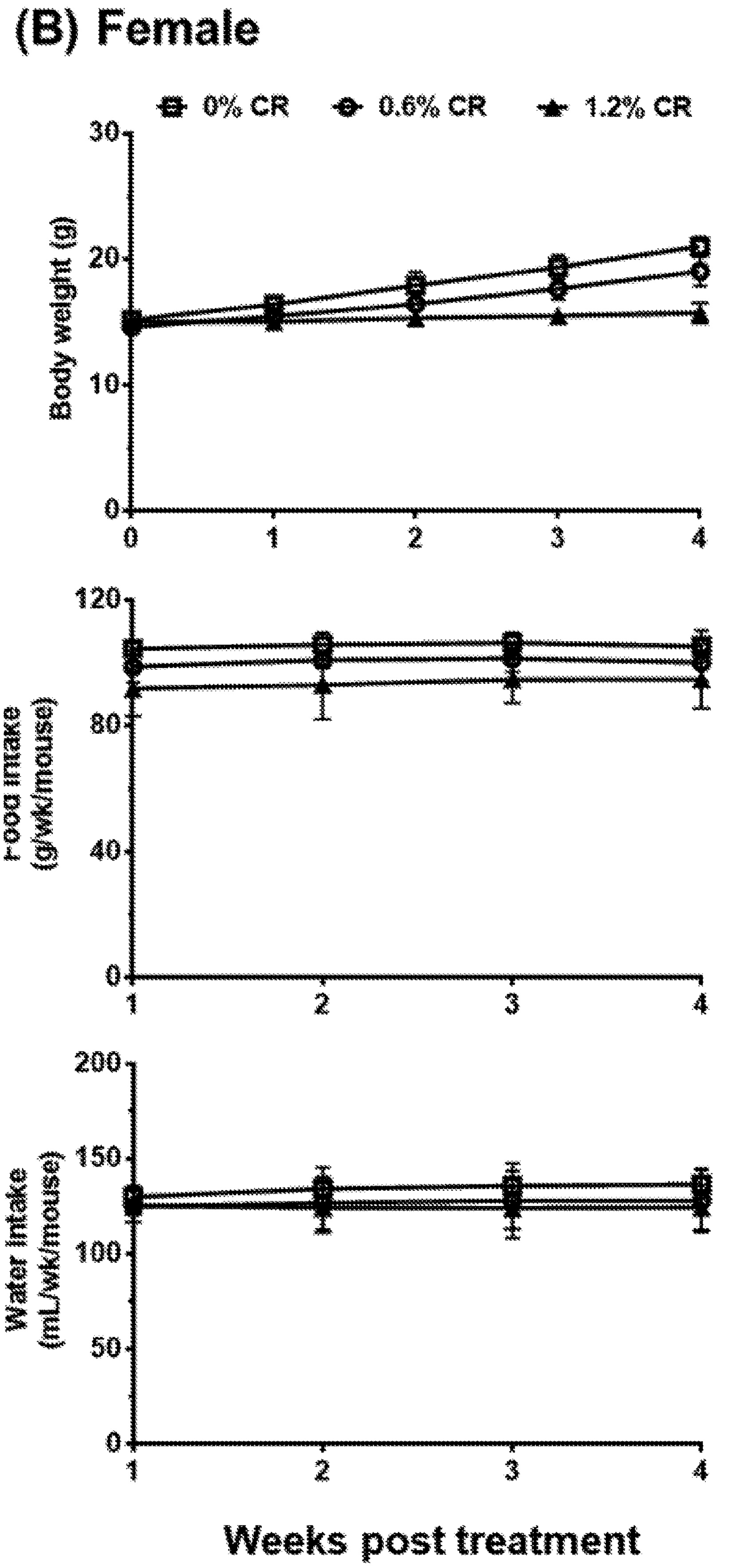
Figure 3:
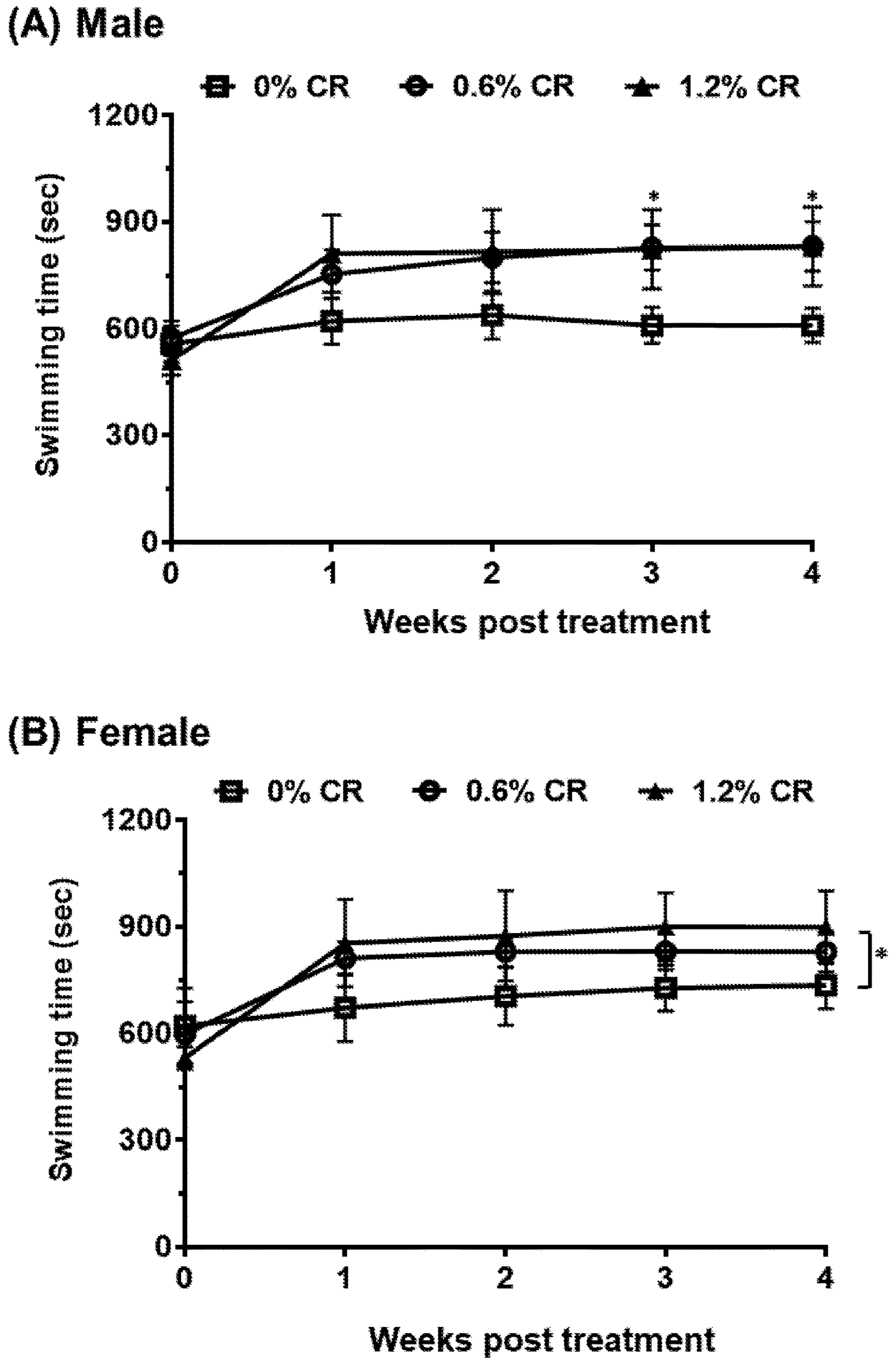
FIGS. 3 (A) and 3 (B) show effect of *Crassocephalum rabens* on exhaustive swimming time of mice. In the program I study, male (A) and female (B) BALB/c mice, aged 4-5 weeks, were randomly assigned into 3 groups (n=5 in each group). One group was fed a standard diet (0% CR), and the other two groups were fed a standard diet containing 0.6% CR and 1.2% CR for 4 weeks. Swimming time was defined as the time from entering the water through floating, struggling and moving until near-drowning due to exhaustion. Values are expressed as the mean±S.D. *p<0.05 as compared with the control group (0% CR), which is considered to be significant.

We prepared chow diet mixed with 0% (control), 0.6% and 1.2% of plant powder of CR and executed the experiment using the program I scheme (FIG. 1). In the program I study, all mice were measured for body weight, food and water intake every week during the experiment period. The body weights of male and female mice given regular diet (0% CR) were increased more significantly than those mice given CR added diet in either high (1.2% CR) or low (0.6% CR) dose (FIGS. 2A and 2B), while feed and water intake amounts within the three groups of mice did not show significant differences (FIGS. 2 (A) and 2 (B)). Notably, the swimming time in the mice given either high or low dose CR was significantly longer than the control group mice in the forced swimming test (FST) (FIGS. 3 (A) and 3 (B)). At the 3rd and 4th weeks after CR diet treatment (either 0.6% CR or 1.2% CR), the total swimming time of CR-treated mice was prolonged 23-26% compared to the control group mice (790-820 sec vs. 610 sec). These results indicate that the CR additive increased the ability of tested mice against fatigue as demonstrated by FST.

CR Extract (CRE) Treatment Increased Forced Swimming Capacity in Mice

Figure 4:
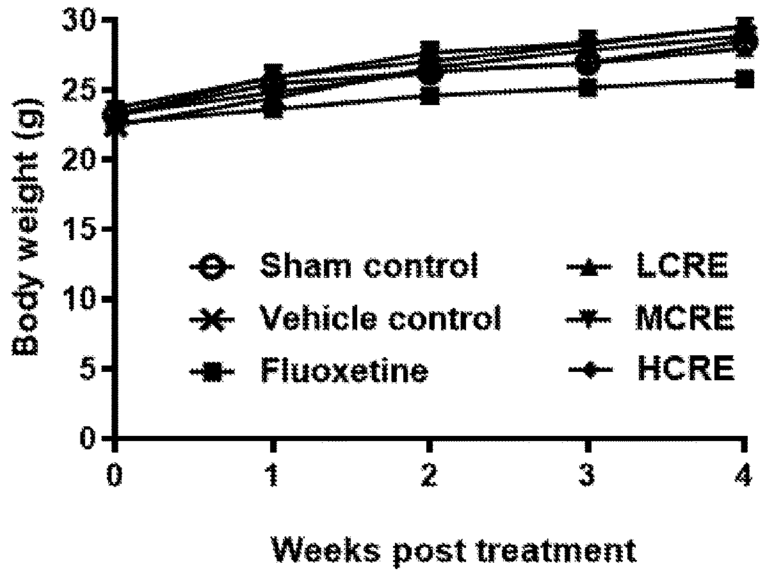
FIG. 4 shows body weight, food consumption and water intake of BALB/c mice fed with *Crassocephalum rabens* extract. Male BALB/c mice, aged 4-5 weeks, were randomly assigned into 6 groups (n=5 in each group). Each mouse was administered with PBS (vehicle control), or *Crassocephalum rabens* extract (CRE) at 150 mg/kg BW (LCRE), 300 mg/kg BW (MCRE), or 600 mg/kg BW (HCRE) through oral administration every day for 4 weeks. Fluoxetine-treated mice were i.p. administered 10 mg/kg every day for 4 weeks. The body weight, food consumption and water intake data were recorded every week for up to 4 weeks.
Figure 4:
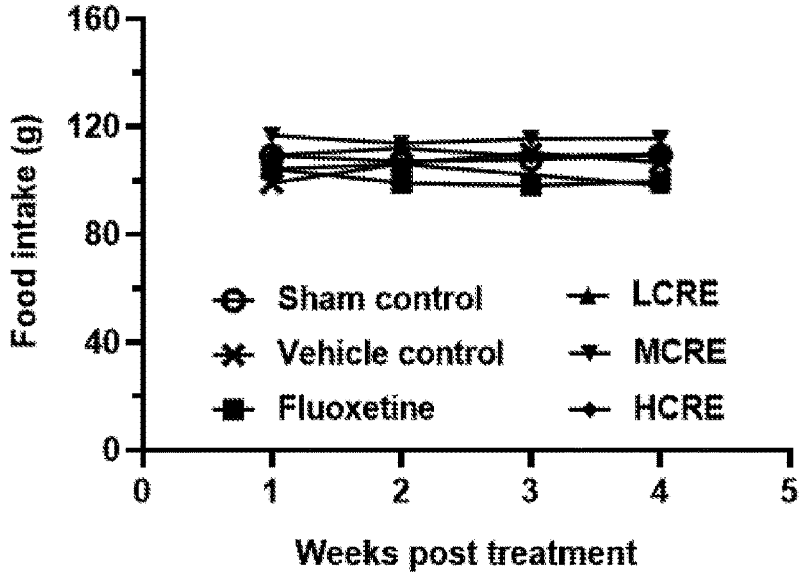
Figure 4:
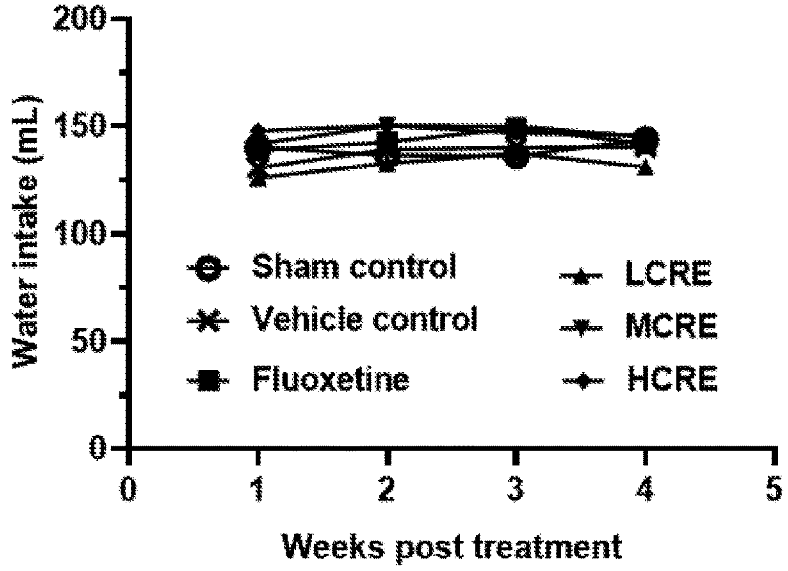
Figure 5:
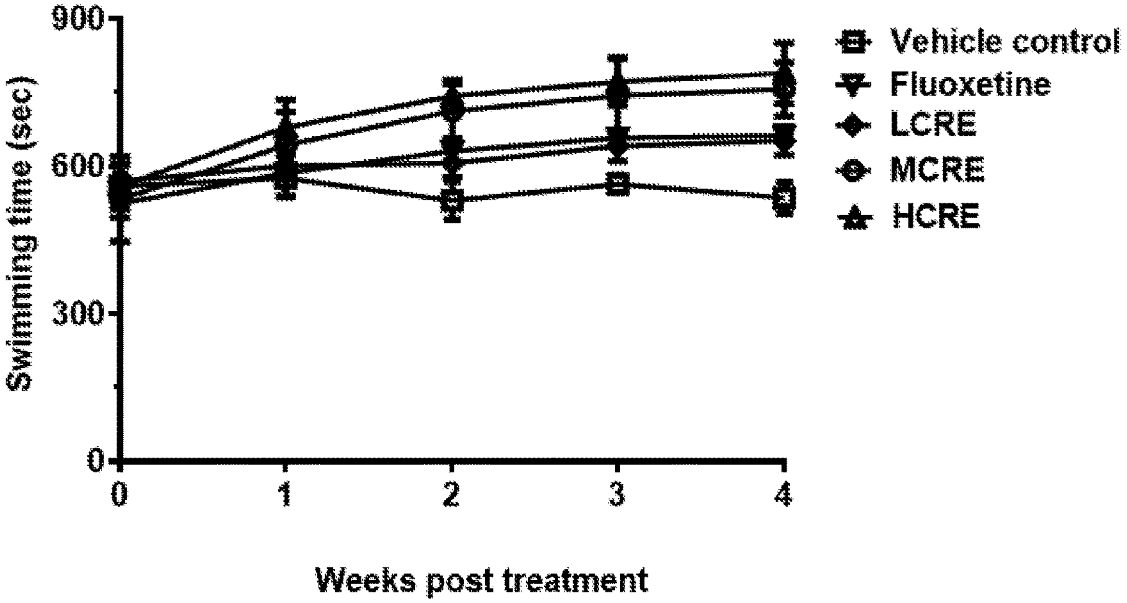
FIG. 5 shows effect of *Crassocephalum rabens* extract on exhaustive swimming time of BALB/c mice examined. Male (BALB/c mice, aged 4-5 weeks, were randomly assigned into each treatment group (n=5 in each group). Each mouse was administered with PBS (vehicle control), or *Crassocephalum rabens* extract (CRE) at 150 mg/kg BW (LCRE), 300 mg/kg BW (MCRE), or 600 mg/kg BW (HCRE) through oral administration every day for 4 weeks. Fluoxetine-treated mice were i.p. administered 10 mg/kg every day for 4 weeks. The exhaustive swimming test was done every week for up to 4 weeks. Values are expressed as the mean±S.D. using one-way ANOVA and *p<0.05 as compared with the vehicle control group.
Figure 5:
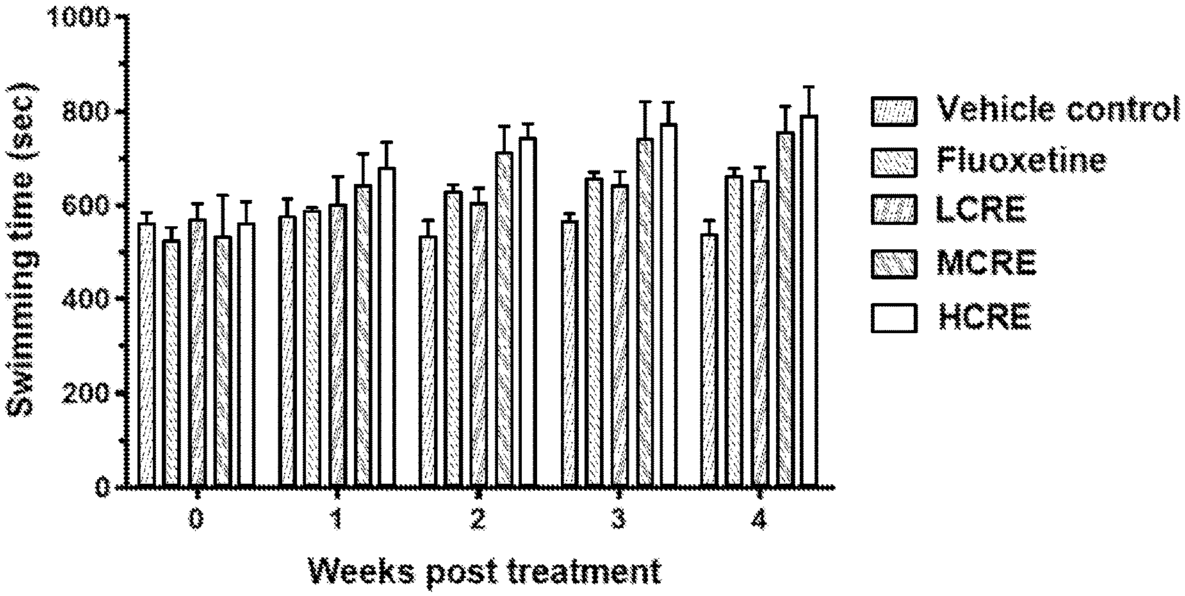

In the program II study, male mice were fed with the CR extract (CRE) at three doses, i.e., 150 mg/kg (LCRE), 300 mg/kg (MCRE), and 600 mg/kg (HCRE) by oral gavage, or i.p. injection with Fluoxetine (10 mg/kg) every day. Our data shows that the body weight, feed and water intake did not have significant differences between the five groups of animals (FIG. 4). Of note, the total swimming time in week 4 of the male mice treated with 150, 300 and 600 mg/kg CRE was 651, 756 and 789 sec, respectively, and mice treated with the control drug Fluoxetine was 662 sec. The vehicle control mice had a similar total swimming time (approximately of 536 sec) in week 0 to week 4. Our results show that mice with LCRE treatment had similar swimming ability to that of the Fluoxetine-treated mice, and better than the vehicle control mice ($p<0.05$). Of note, at week 4, MCRE and HCRE treatments prolonged swimming time to approximately 30-32% longer than the vehicle treatment (756-789 sec vs. 536 sec) and 12-16% longer than the Fluoxetine drug (756-789 sec vs. 662 sec) (FIG. 5). A commercial chicken essence product administered 50 mg/kg/day (p.o.) showed a similar effect with respect to the LCRE, but shorter swimming times than the MCRE and HCRE (data not shown). These results indicate significant anti-fatigue effects of the MCRE/HCRE which are better than the control drug Fluoxetine as evaluated by forced swimming experiments.

Figure 6:
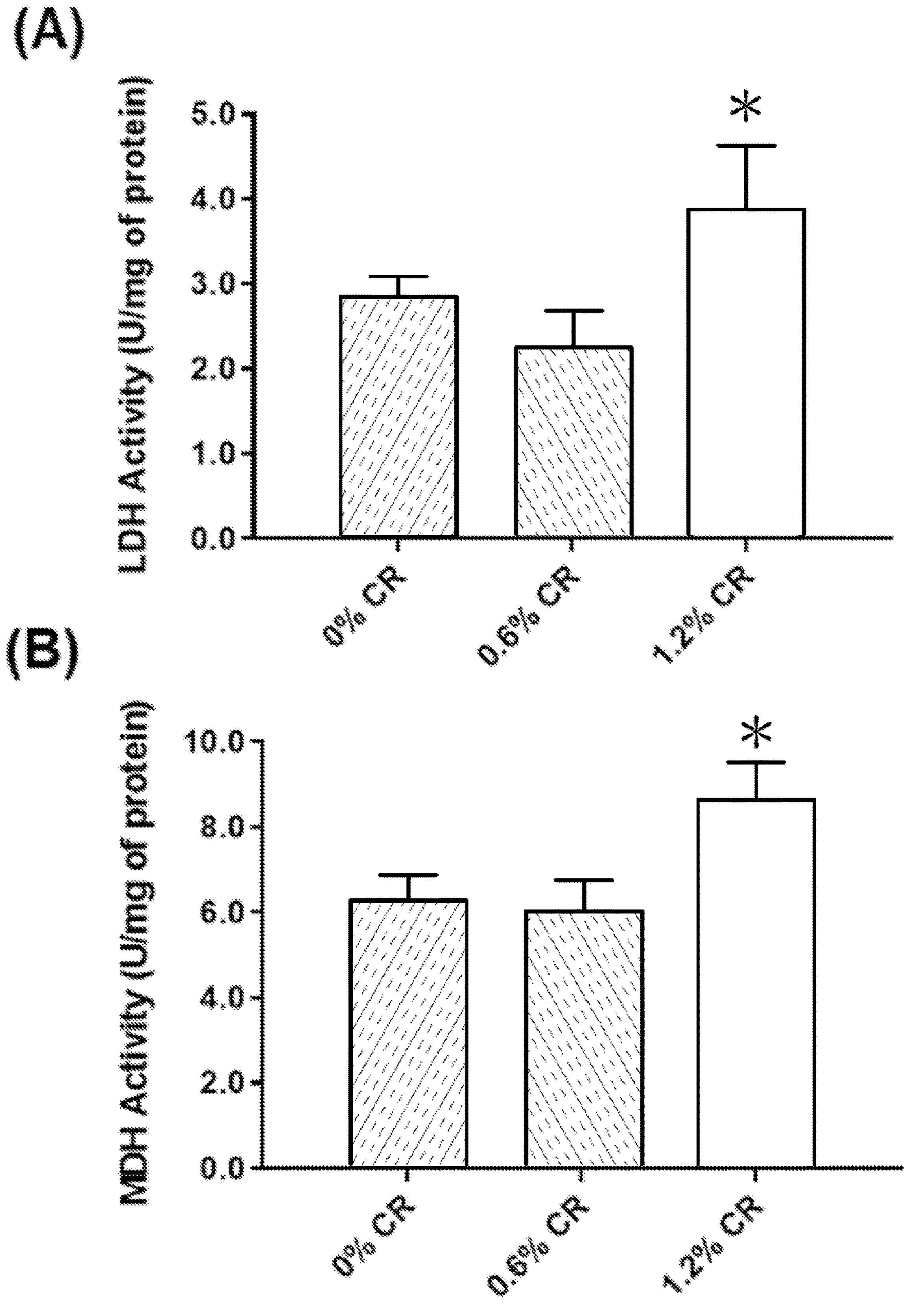
FIGS. 6 (A) and 6 (B) show effect of *Crassocephalum rabens* feed additives on skeletal muscle lactate dehydrogenase (LDH) and muscle malate dehydrogenase (MDH) activities in male BALB/c mice after force swimming test (Program I). Male BALB/c mice, aged 4-5 weeks, were randomly assigned into 3 groups (n=5 in each group). One group was fed a standard diet (0% CR), and the other two groups were fed with standard diet containing 0.6% CR and 1.2% CR for 4 weeks. A mice force swimming test (FST) was done once a week. Total proteins of skeletal muscle were extracted and LDH activity (A) and MDH activity (B) were determined in the end of experiment. Data are expressed as the mean±S.D. and *p<0.05 as compared with the control group (0% CR), which is considered to be significant.
Figure 7:
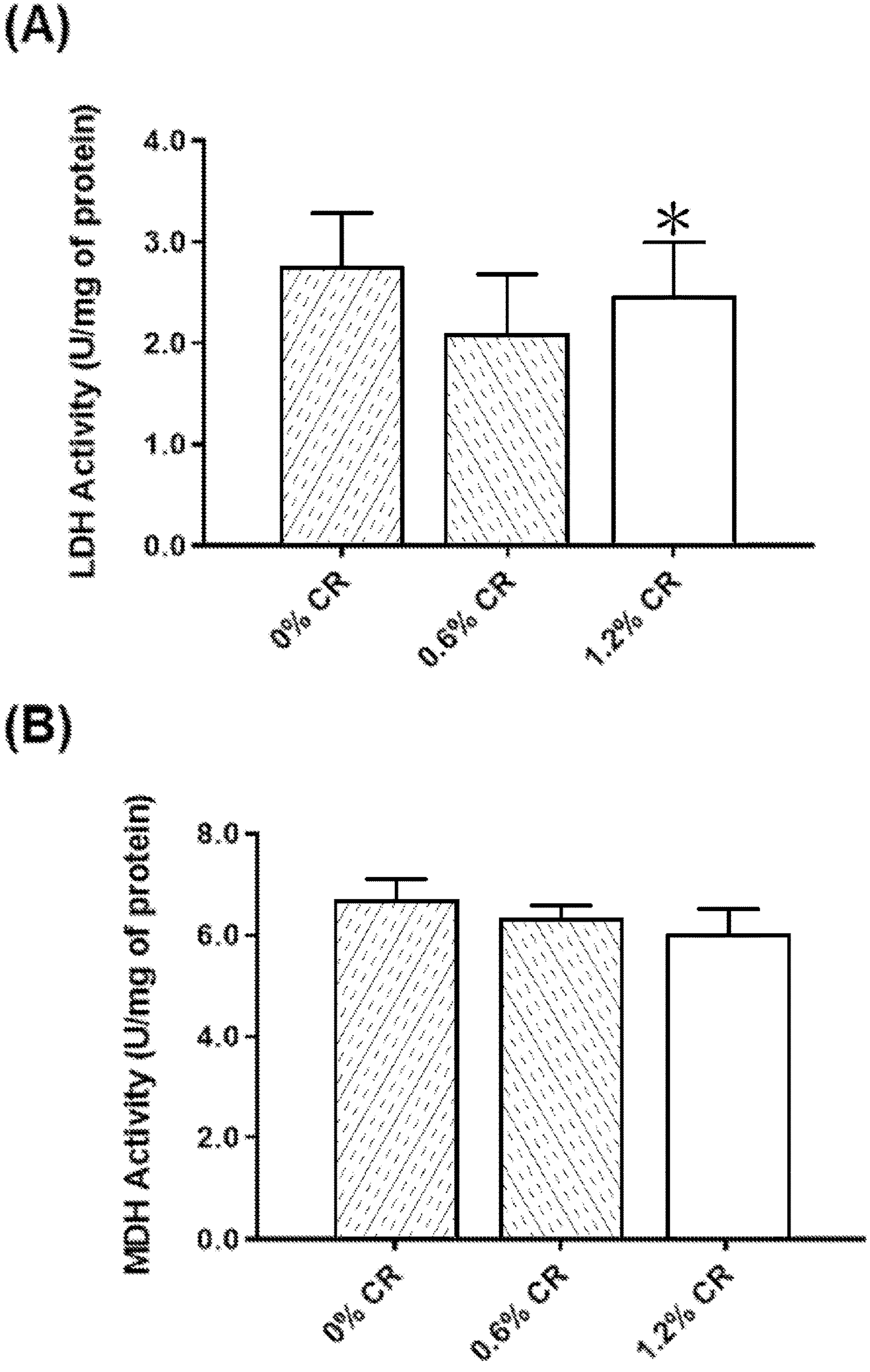
FIGS. 7 (A) and 7 (B) show effect of *Crassocephalum rabens* feed additives on muscle lactate dehydrogenase (LDH) and muscle malate dehydrogenase (MDH) activities in female BALB/c mice after force swimming test (Program I). Female BALB/c mice, aged 4-5 weeks, were randomly assigned into 3 groups (n=5 in each group). One group was fed a standard diet (0% CR), and the other two groups were fed a standard diet containing 0.6% CR and 1.2% CR for 4 weeks. A mice force swimming test (FST) was done once a week. Total proteins of skeletal muscle were extracted and LDH activity (A) and MDH activity (B) were determined in the end of experiment. Data are expressed as the mean±S.D. and *p<0.05 as compared with the control group (0% CR), which is considered to be significant.
Figure 8:
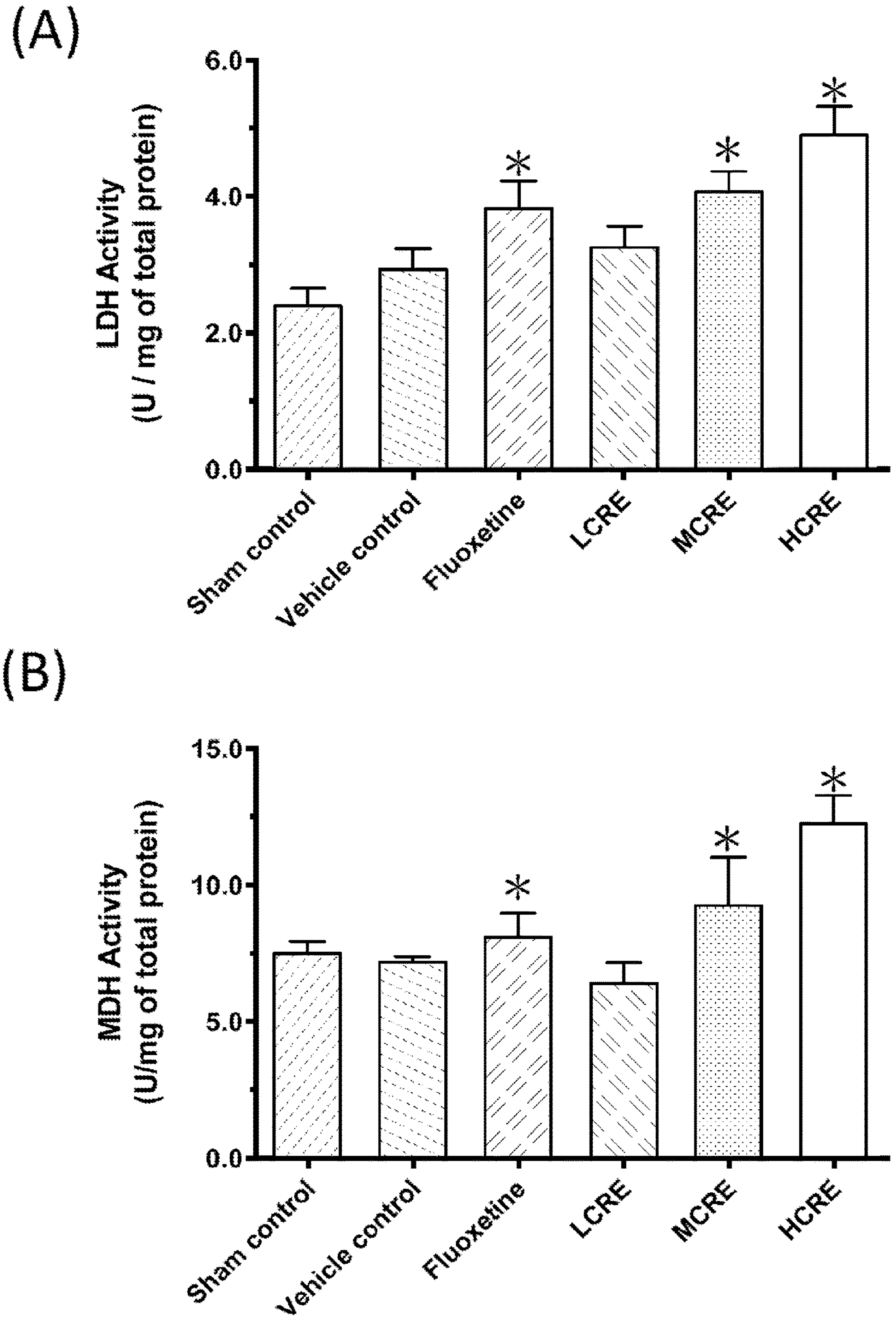
FIGS. 8 (A) and 8 (B) show effect of oral gavage *Crassocephalum rabens* extract on lactate dehydrogenase (LDH) and malate dehydrogenase (MDH) activities in skeletal muscle in BALB/c mice (Program II). Male BALB/c mice, aged 4-5 weeks, were randomly assigned into 6 groups (n=5 in each group). Each mouse was administered with PBS (vehicle control), or *Crassocephalum rabens* extract (CRE) at 150 mg/kg BW (LCRE), 300 mg/kg BW (MCRE), or 600 mg/kg BW (HCRE) through oral administration every day for 4 weeks. Fluoxetine-treated mice were i.p. administered 10 mg/kg every day for 4 weeks. The LDH and MDH activities in skeletal muscle was determined at the $4^{th}$ week. Values are expressed as the mean±S.D. using one-way ANOVA and *p<0.05 as compared with the control group (vehicle control).

CR or CRE Treatment Increased Skeletal Muscle LDH and MDH Activities in Male Mice In most cases, skeletal muscle needs energy during exercise. Glycogen acts as the primary source of energy for exercise, during which time lactate accumulates in the myofibril. Here, we used LDH, MDH and glycogen levels as an index to evaluate the efficacy of *C. rabens* in skeletal muscle during the forced swimming test. When male mice completed the exercise in program I, LDH (FIG. 6 (A)) and MDH (FIG. 6 (B)) activities had increased significantly by 30% in the high dose CR (1.2% CR) group compared to the control group ($p<0.05$); however, there were no significant differences in the LDH or MDH activities observed in the female mice fed with the control diet or CR diet (FIG. 7 (A) and FIG. 7 (B)). Skeletal muscle LDH and MDH activities of male mice in program II showed significant and dose-dependent increases by CRE treatment. The MCRE and HCRE oral feeding mice have increased 1.4-2.3-fold of the LDH activities (FIG. 8 (A)) and 1.8-2.3-fold of the MDH activities (FIG. 8 (B)) compared to the vehicle control group. The positive control drug Fluoxetine treatment increased 1.3-fold and 1.1-fold in the LDH and MDH activities, respectively, as compared to the vehicle control treatment. The skeletal muscle glycogen levels, however, did not show significant difference between CR and control groups, or CRE and control groups (data not shown), suggesting CR or its derived extract do not affect glycogen levels in mice with or without swimming exercise. Together, CR and CRE significantly increased the LDH and MDH activities in the forced swimming male mice that are better than the effects of the anti-depressant drug Fluoxetine.

Clinical Biochemistry

Serum samples of the mice oral gavaged with different doses of CR for 28 days were collected for determination of clinical biochemical parameters. The data are summarized in Table 1. The levels of glutamate oxaloacetate transaminase (GOT), glutamate pyruvate transaminase (GPT), alkaline phosphatase (ALP), total protein (TP), albumin (ALB), blood urine nitrogen (BUN), creatinine (CTE), lactate dehydrogenase (LDH), and creatine phosphokinase (CPK) showed no statistical significances between the control and CR-fed mice (Table 1). Further, the various biochemical parameters of male mice sera after oral feeding with CRE or i.p. administration with the anti-depressant drug Fluoxetine for 28 days that showed no significant difference and fall within the reference range of normal or healthy mice (Table 2). These results suggest that *C. rabens* plant and derived extract at the tested doses did not have a concern of toxicity in animals.

TABLE 1

Biochemical parameters of mice sera after oral feeding with *Crassocephalum rabens* plants (CR) for 28 days.

| | Male | | | Female | | | References |
|---|---|---|---|---|---|---|---|
| Paramter | 0% CR | 0.6% CR | 1.2% CR | 0% CR | 0.6% CR | 1.2% CR | Range |
| GOT(U/L) | 151.5 ± 14.5 | 89.0 ± 26.0 | 135.5 ± 36.5 | 102.0 ± 9.0 | 283.0 ± 70.0 | 276.0 ± 65.0 | 55.0-352.0 |
| GPT(U/L) | 45.5 ± 9.5 | 38.0 ± 11.0 | 37.5 ± 8.5 | 33.5 ± 7.5 | 111.0 ± 17.0 | 86.5 ± 9.5 | 14.3-181.3 |
| LDH(U/L) | 347.5 ± 45.5 | 271.9 ± 67.5 | 351.5 ± 149.5 | 308.4 ± 29.0 | 346.7 ± 52.85 | 209.5 ± 74.5 | 213.05-353.95 |
| ALP(U/L) | 414.5 ± 34.5 | 389.5 ± 12.0 | 424.0 ± 46.0 | 336.0 ± 61.0 | 385.0 ± 21.5 | 411.5 ± 58.5 | 118.0-433.0 |
| GLU(mg/dL) | 217.0 ± 14.0 | 266.5 ± 22.5 | 240.5 ± 74.5 | 238.5 ± 13.5 | 266.5 ± 15.5 | 207.5 ± 3.5 | 129.0-329.0 |
| BUN(mg/dL) | 20.45 ± 0.85 | 24.55 ± 3.15 | 20.00 ± 1.10 | 33.95 ± 0.15 | 34.35 ± 0.05 | 29.65 ± 2.65 | 7.0-31.0 |
| CTE(mg/dL) | 0.65 ± 0.25 | 0.20 ± 0.00 | 0.20 ± 0.00 | 0.35 ± 0.05 | 0.25 ± 0.05 | 0.15 ± 0.05 | 0.2-0.5 |
| UA(mg/dL) | 3.50 ± 0.50 | 5.40 ± 0.50 | 5.00 ± 1.00 | 3.65 ± 0.85 | 6.70 ± 1.50 | 2.65 ± 0.15 | 2.54-3.46 |
| CHO(mg/dL) | 149.0 ± 4.0 | 157.5 ± 18.5 | 145.0 ± 13.0 | 98.5 ± 2.5 | 143.5 ± 12.5 | 124.0 ± 12.0 | 81.0-208.0 |
| HDL(mg/dL) | 62.7 ± 4.3 | 57.9 ± 12.8 | 64.80 ± 4.7 | 55.1 ± 5.9 | 48.32 ± 12.3 | 55.70 ± 10.5 | 47.15-64.65 |
| TG(mg/dL) | 282.0 ± 1.0 | 218.0 ± 31.0 | 147.5 ± 7.5 | 154.5 ± 23.5 | 239.5 ± 20.5 | 260.5 ± 96.5 | 107.0-535.0 |
| TBIL(mg/dL) | 0.50 ± 0.00 | 0.65 ± 0.05 | 0.80 ± 0.20 | 0.70 ± 0.00 | 0.85 ± 0.05 | 0.90 ± 0.10 | 0.50-0.80 |
| TP(g/dL) | 5.40 ± 0.10 | 5.90 ± 0.20 | 5.60 ± 0.20 | 5.05 ± 0.35 | 5.95 ± 0.35 | 5.30 ± 0.20 | 4.9-7.3 |
| ALB(g/dL) | 2.80 ± 0.00 | 3.20 ± 0.00 | 2.65 ± 0.15 | 2.90 ± 0.10 | 3.35 ± 0.25 | 2.80 ± 0.20 | 2.1-4.1 |
| GLOB(g/dL) | 2.60 ± 0.10 | 2.70 ± 0.20 | 2.95 ± 0.05 | 2.15 ± 0.25 | 2.60 ± .010 | 2.50 ± 0.00 | 2.1-2.7 |
| A/G ratio | 1.08 ± 0.04 | 1.19 ± 0.09 | 0.09 ± 0.04 | 1.36 ± 0.11 | 1.29 ± 0.05 | 1.12 ± 0.08 | 0.33-1.93 |

Blood samples of control or treated male mice were analyzed after the 28-day treatment. The data are expressed as mean±S.D. Statistical comparisons of the control (0% CR) and CRE-fed mice were performed by one-way ANOVA with the Tukey multiple range test. P values are calculated in relation to the control group. Abbreviations: GOT, glutamic oxaloacetic transaminase; GPT, glutamic pyruvic transaminase; LDH, lactate dehydrogenase; ALP, alkaline phosphatase; GLU, glucose; BUN, blood urea nitrogen; CTE, creatinine; UA, uric acid; CHO, cholesterol; HIDL, high-density lipoprotein; TG, triglyceride; TBTL, total bilirubin; TP, total protein; ALB, albumin; GLOB, globulin; A/G ratio, albumin-globulin in ratio; and Reference range: https://www.envigo.com/products-services/research-models-services/models/research-models/mice/inbred/balb-c-inbred-mice/, https://www.criver.com/sites/default/files/resources/BALBcMouseClinicalPathologyData.pdf

TABLE 2

Biochemical parameters of male mice sera after oral feeding with *Crassocephalum rabens* extracts (CRE) for 28 days.

| Paramter | Sham control | Vehicle control | Fluoxetine | LCRE | MCRE | HCRE | References Range |
|---|---|---|---|---|---|---|---|
| GOT(U/L) | 139.5 ± 17.5 | 152.0 ± 14.0 | 171.0 ± 19.8 | 106.0 ± 8.0 | 187.0 ± 106.1 | 205.8 ± 88.5 | 55.0-352.0 |
| GPT(U/L) | 58.5 ± 8.3 | 49.5 ± 8.5 | 61.2 ± 19.2 | 37.5 ± 9.5 | 81.3 ± 39.9 | 64.0 ± 22.3 | 14.3-181.3 |
| LDH(U/L) | 383.5 ± 12.2 | 405.0 ± 67.5 | 362.7 ± 65.3 | 236.5 ± 110.5 | 332.5 ± 135.1 | 404.8 ± 43.2 | 213.05-455.0 |
| ALP(U/L) | 541.5 ± 37.7 | 512.0 ± 33.0 | 501.2 ± 21.2 | 587.0 ± 14.0 | 547.5 ± 23.0 | 420.8 ± 116.1 | 118.0-544.0 |
| GLU(mg/dL) | 264.0 ± 18.7 | 212.0 ± 14.0 | 207.0 ± 12.6 | 226.5 ± 10.5 | 264.0 ± 14.7 | 222.8 ± 51.3 | 129.0-329.0 |
| BUN(mg/dL) | 24.2 ± 0.2 | 20.25 ± 1.35 | 20.05 ± 2.01 | 34.10 ± 0.60 | 29.45 ± 5.44 | 24.93 ± 4.99 | 7.0-31.0 |
| CTE(mg/dL) | 0.20 ± 0.00 | 0.70 ± 0.20 | 0.45 ± 0.05 | 0.45 ± 0.05 | 0.25 ± 0.05 | 0.23 ± 0.04 | 0.2-0.5 |
| UA(mg/dL) | 3.14 ± 0.35 | 3.75 ± 0.35 | 2.77 ± 0.32 | 3.65 ± 0.55 | 2.85 ± 0.25 | 3.22 ± 0.45 | 2.54-3.46 |
| CHO(mg/dL) | 175.5 ± 7.2 | 153.0 ± 6.0 | 136.5 ± 42.9 | 107.5 ± 6.5 | 150.5 ± 18.9 | 135.8 ± 18.1 | 81.0-208.0 |
| HDL(mg/dL) | 133.6 ± 11.5 | 134.5 ± 13.5 | 136.6 ± 15.3 | 96.5 ± 4.5 | 127.8 ± 19.1 | 99.8 ± 28.1 | 56.1-155.0 |
| TG(mg/dL) | 186.5 ± 5.5 | 289.0 ± 3.0 | 288.3 ± 27.1 | 165.5 ± 20.5 | 229.8 ± 25.4 | 208.5 ± 92.0 | 107.0-535.0 |
| TBIL(mg/dL) | 0.65 ± 0.02 | 0.55 ± 0.05 | 0.65 ± 0.04 | 0.75 ± 0.05 | 0.75 ± 0.11 | 0.85 ± 0.11 | 0.50-0.80 |
| TP(g/dL) | 6.10 ± 0.11 | 5.55 ± 0.05 | 5.01 ± 0.35 | 5.25 ± 0.35 | 5.98 ± 0.38 | 5.43 ± 0.33 | 4.9-7.3 |
| ALB(g/dL) | 3.10 ± 0.07 | 2.80 ± 0.00 | 3.67 ± 0.28 | 2.95 ± 0.25 | 3.35 ± 0.18 | 2.78 ± 0.18 | 2.1-4.1 |
| GLOB(g/dL) | 3.00 ± 0.04 | 2.75 ± 0.05 | 2.01 ± 0.21 | 2.30 ± 0.10 | 2.63 ± 0.26 | 2.65 ± 0.23 | 2.1-3.0 |
| A/G ratio | 1.03 ± 0.01 | 1.02 ± 0.02 | 1.04 ± 0.12 | 1.28 ± 0.05 | 1.29 ± 0.11 | 1.05 ± 0.10 | 0.33-1.93 |

Blood samples of control or treated male mice were analyzed after the 28-day treatment. The data are expressed as mean±S.D. Statistical comparisons of the control (0% CR) and CRE-fed mice were performed by one-way ANOVA with the Tukey multiple range test. P values are calculated in relation to the control group. Abbreviations: GOT, glutamic oxaloacetic transaminase; GPT, glutamic pyruvic transaminase; LDH, lactate dehydrogenase; ALP, alkaline phosphatase; GLU, glucose; BUN, blood urea nitrogen; CTE, creatinine; UA, uric acid; CHO, cholesterol; HDL, high-density lipoprotein; TG, triglyceride; TBIL, total bilirubin; TP, total protein; ALB, albumin; GLOB, globulin; A/G ratio, albumin-globulin in ratio; and Reference range: https://www.envigo.com/products-services/research-models-services/models/research-models/mice/inbred/balb-c-inbred-mice/, https://www.criver.com/sites/default/files/resources/BALBcMouseClinicalPathologyData.pdf

CONCLUSIONS

In the present study, we assessed the antifatigue activity of *C. rabens*, either plant powder or extract, by measuring exhaustive swimming time and the skeletal muscle levels of indicators related to physical fatigue. Our animal experimental results show that *C. rabens* reveals a potent anti-fatigue function, as evidenced by extending the exhaustive swimming time of the treated mice longer than the control mice by 32%, and the anti-depressant drug Fluoxetine-treated mice by 16%. The anti-fatigue activity of *C. rabens* appears to be closely associated with skeletal muscle LDH and MDH activities, but not directly related to muscle glycogen content. Taken together, our results suggest that *C. rabens* could be used to prevent fatigue that might be associated with anti-depressant effects.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A method for ameliorating or treating depression-associated muscle fatigue in a subject in need thereof, said method comprising administering to said subject a composition comprising:

(a) a therapeutically effective amount of dried *Crassocephalum rabens* plant or an extract of a fresh pressed liquid of *Crassocephalum rabens*; and (b) a pharmaceutically acceptable carrier or excipient;

wherein said administering of the composition increases muscular endurance in the subject after administration to the subject for a period of time relative to an untreated control;

wherein the muscular endurance is optionally characterized by increased skeletal muscle lactate dehydrogenase and/or malate dehydrogenase activity; and wherein the plant is *Crassocephalum rabens* at the flower blooming stage.

2. The method according to claim 1, wherein the *Crassocephalum rabens* is *Crassocephalum rabens* S. Moore, *Crassocephalum crepidioides* S. Moore, or *Crassocephalum crepidioides*.

3. The method according to claim 1, wherein the subject further suffers from a disease, disorder or condition selected from the group consisting of multiple sclerosis, Parkinson's disease, Alzheimer's disease, chronic fatigue syndrome, fibromyalgia, chronic pain, traumatic brain injury, AIDS, and osteoarthritis.

4. The method according to claim 1, wherein the muscle fatigue is associated with a particular treatment or therapy used to treat a disease, disorder, or condition, including, without limitation, chemotherapy, radiation therapy, bone marrow transplant, and anti-depressant medications.

5. The method according to claim 1, wherein the muscle fatigue is chronic or acute muscle fatigue.

6. The method according to claim 1, wherein the *Crassocephalum rabens* plant further comprises a galactolipid compound selected from the group consisting of 1,2-di-O-α-linolenoyl-3-O-β-galactopyranosyl-sn-glycerol and 1,2-di-(α-linolenoyl)-3-[α-D-galactosyl-(1-6)-β-D-galactosyl]-sn-glycerol.

* * * * *